United States Patent [19]
Josefowicz

[11] Patent Number: 4,769,509
[45] Date of Patent: Sep. 6, 1988

[54] REDUCIBLE METAL OXIDE COMPOSITIONS CONTAINING ZIRCONIUM

[75] Inventor: Jack Y. Josefowicz, Westlake Village, Calif.

[73] Assignee: Atlantic Richfield Company, Los Angeles, Calif.

[21] Appl. No.: 919,540

[22] Filed: Oct. 16, 1986

Related U.S. Application Data

[62] Division of Ser. No. 759,005, Jul. 25, 1985, Pat. No. 4,656,155.

[51] Int. Cl.$^4$ ................................................ C07C 2/00
[52] U.S. Cl. .................................... 585/500; 585/415; 585/417; 585/418; 585/629; 585/654; 585/656; 585/661; 585/700; 585/943
[58] Field of Search ............... 585/500, 417, 415, 418, 585/654, 661, 658, 541, 700, 943

[56] References Cited

U.S. PATENT DOCUMENTS

| 4,239,658 | 12/1980 | Mitchell, III et al. | 585/500 |
| 4,450,310 | 5/1984 | Fox et al. | 585/500 |
| 4,499,323 | 2/1985 | Gaffney | 585/500 |
| 4,499,324 | 2/1985 | Gaffney | 585/500 |
| 4,523,049 | 6/1985 | Jones et al. | 585/500 |
| 4,547,608 | 10/1985 | Johnson | 585/500 |
| 4,608,449 | 8/1986 | Baerns et al. | 585/500 |

Primary Examiner—William R. Dixon, Jr.
Assistant Examiner—James M. Hunter, Jr.
Attorney, Agent, or Firm—Craig E. Larson

[57] ABSTRACT

A class of mixed oxide catalysts comprising at least one reducible metal oxide, which oxide produces higher hydrocarbons and water when contacted with a hydrocarbon at synthesizing conditions, at least one oxide of zirconium, and at least one oxide of yttrium. The compositions are useful for hydrocarbon conversion, methane conversion, and oxidative dehydrogenation processes characterized by the formation of coproduct water.

14 Claims, No Drawings

REDUCIBLE METAL OXIDE COMPOSITIONS CONTAINING ZIRCONIUM

This is a division of application Ser. No. 759,005, filed July 25, 1985, now U.S. Pat. No. 4,656,155.

BACKGROUND OF THE INVENTION

The present invention relates to compositions comprising metal oxide and oxides of zirconium and yttrium. The present invention also relates to hydrocarbon conversion processes employing reducible metal oxide supported by zirconium and yttrium compositions. In one particular aspect, it relates to methods for converting methane to higher hydrocarbons. In another particular aspect, it relates to processes for the oxidative dehydrogenation of hydrocarbons, especially to processes for the oxidative dehydrogenation of paraffinic hydrocarbons to the corresponding mono-olefins. The central aspect of the presently claimed invention is the catalyst compositions employed in such hydrocarbon conversion processes.

Hydrocarbon conversion processes employing the compositions of this invention are characterized by relatively severe reaction conditions and by the formation of coproduct water. Thus, hydrothermal stability at elevated temperatures (e.g., 500° to 1000° C.) is an important criterion for the compositions. Moreover, uses contemplated for the present compositions require catalysts which are rugged, attrition resistant, and stable at high temperatures. It is also desirable that the compositions are able to operate effectively for relatively long periods while cycling between oxidized and reduced states.

An object of the present invention is a composition and process for hydrocarbon conversion processes, especially for processes characterized by the formation of byproduct water. A related object is a rugged, attrition resistant and stable oxidant composition for such processes.

Another object of the present invention is a composition and process for converting methane to higher hydrocarbons, especially for processes characterized by the formation of byproduct water.

Still another object of the present invention is a composition and process for the oxidative dehydrogenation of hydrocarbons. Another related object is a composition and process for the oxidative dehydrogenation of paraffinic hydrocarbons to form the corresponding mono-olefins.

Other objects, aspects and advantages of the present invention will become apparent to those skilled in the art upon studying this Specification and the appended claims.

SUMMARY OF THE INVENTION

This invention is a class of catalyst compositions comprising:
(a) at least one reducible metal oxide;
(b) oxide of zirconium; and
(c) oxide of yttrium.

The compositions of this invention are useful in a variety of hydrocarbon conversion processes. When the active form of the composition (i.e., the composition in an oxidized state) is contacted with methane at elevated temperatures (e.g., at temperatures within the range of about 500° to about 1000° C.), methane is converted to higher hydrocarbons. The compositions are also effective contact agents (i.e., catalysts) in oxidative dehydrogenation processes.

DETAILED DESCRIPTION OF THE INVENTION

While the compositions of the present invention are referred to as "catalyst", it will be understood that, under conditions of use, this catalyst serves as a selective oxidant and, therefore, takes on the characteristics of a reactant during use.

In the following formulas describing the compositions of this invention, the relative number of oxygens is designated by "x". This x is variable because the compositions may continually gain and lose oxygen during use. Thus, setting a strict range of values for x would be imprecise and possibly misleading. Generally, the value ascribed to x falls within the range of the number of oxygens required in the higher oxidation states (the "active" or "oxidized" composition) to the number of oxygens required in the lower oxidation states (the "reduced" composition).

The principal component of the compositions is described as "reducible metal oxide". This term is meant to embrace both reducible oxides of metal and reduced oxides of metal, it being understood that reducible oxides of metal comprise the principal active component of the compositions. Then, in its active state, the present composition comprises at least one reducible metal oxide, which oxide produces higher hydrocarbons (or, in the case of higher hydrocarbon dehydrogenation, dehydrogenated hydrocarbons), coproduct water, and a reduced metal oxide when contacted with methane (or higher hydrocarbons) at synthesizing (or dehydrogenation) conditions (e.g., at a temperature within the range of about 500° to about 1000° C.). The term "reducible" is used to identify those metal oxides which are reduced under the aforesaid conditions. The term "reducible metal oxides" includes: (1) compounds described by the general formula $M_xO_y$ wherein x and y designate the relative atomic proportions of metal and oxygen in the composition and/or (2) one or more oxygen-containing metal compounds (i.e., compounds containing elements in addition to metal and oxygen); provided that such oxides and compounds have the capability of producing higher hydrocarbons from methane or of producing dehydrogenated hydrocarbons from dehydrogenatable hydrocarbons as described herein.

Reducible metal oxides suitable for the compositions of this invention include manganese, tin, indium, germanium, antimony, lead, bismuth, praseodymium, terbium, cerium, iron, and ruthenium. The preferred metal oxide is manganese. Preferably, the composition of this invention comprises zirconia from about 1 to about 40 percent and yttria from about 1 to about 15 weight percent. More preferably, the yttria ranges from about 2 to about 10 weight percent.

One class of preferred compositions is characterized by the substantial absence of catalytically effective amounts of nickel and the noble metals (e.g., rhodium, palladium, silver, osmium, iridium, platinum, and gold), and compounds thereof to minimize the deleterious catalytic effects of such metals and compounds thereof. For example, at the conditions (e.g., temperatures) under which the present compositions are used, these metals tend to promote coke formation and oxides of these metals tend to promote the formation of combustion products ($CO_x$), rather than the desired hydrocarbons. The term "catalytically effective" is used to identify that quantity of nickel, the noble metals, and compounds thereof which, when present, substantially changes the distribution of products obtained when employing the compositions of this invention.

Preferably, the compositions of this invention comprise additionally an alkali metal component. Other additives may also be incorporated into the compositions of this invention. For example, the addition of a phosphorus component has been found to enhance the stability of the compositions. When used, phosphorus may be present up to an amount providing a phosphorus-to-manganese ratio of about 2:1. If phosphorus is employed, it is desirable to provide it during catalyst preparation in the form of phosphates of alkali metals (e.g., orthophosphates, metaphosphates and pyrophosphates). Pyrophosphates are preferred. Sodium pyrophosphate is particularly preferred. Phosphorus can be provided in other forms though. Examples include orthophosphoric acid, ammonium phosphates, and ammonium hydrogenphosphates.

Further examples of other components which may be present in the compositions of this invention are halogen and chalcogen components. Such components may be added either during preparation of the catalyst or during use.

CATALYST COMPOSITIONS

The broad class of compositions within the scope of this invention comprises:
(a) at least one reducible metal oxide;
(b) oxide of zirconium; and
(c) oxide of yttrium.

The amount of reducible metal oxide present is preferably within the range of about 1 to about 40 weight percent based on the total weight of the composition, more preferably within the range of about 5 to about 30 weight percent.

The catalysts of this invention are conveniently prepared by any of the methods associated with similar compositions known in the art. Thus, methods such as precipitation, co-precipitation, impregnation, granulation, spray drying or dry mixing can be used. The reducible metal oxide can be composited or associated with the zirconium and yttrium components of the compositions by any of the methods associated with the preparation of supported catalyst compositions known in the art. Such "supported" compositions may be prepared by methods such as adsorption, impregnation, precipitation, co-precipitation, granulation, spray drying or dry mixing. Substantially any compound of the recited components can be employed in the preparation of the compositions.

One suitable method of preparation is to impregnate compounds of the zirconium and ytrrium components of the compositions with solutions of compounds of reducible metal oxide. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides or iodides. After impregnation, the preparation is dried to remove solvent and the dried solid is calcined, preferably in air at a temperature selected within the range of about 300° to about 1200° C. Particular calcination temperatures will vary, depending on the compounds employed.

When an alkali metal is employed, the alkali metal component is preferably provided as a basic composition of the alkali metal(s). Examples are sodium hydroxide, sodium acetate, lithium hydroxide, lithium acetate, etc.

An alternative method of preparation includes the preparation of aqueous slurries of the reducible metal oxide, followed by the addition of solutions containing other catalyst components, then drying and calcining the resulting mixtures. Alternatively, as discussed in the above composition descriptions, the oxides may be provided as preformed compounds, with the other components added as described above.

Regardless of how the components are combined, the resulting composite will generally be dried and calcined at elevated temperatures prior to use.

HYDROCARBON CONVERSION PROCESS

The catalyst compositions of the present invention are generally useful for hydrocarbon conversion processes. Contacting a hydrocarbon feedstock with the active composition produces higher hydrocarbons, coproduct water, and a reduced catalyst composition. The reduced catalyst composition is readily reoxidized to an active state by contact with an oxidant such as air or other oxygen-containing gas. The process may be effected in a cyclic manner wherein the catalyst is contacted alternately with a hydrocarbon feed and then with an oxygen-containing gas. The process may also be effected in a noncyclic manner wherein the catalyst is contacted concurrently with a hydrocarbon feed and an oxygen-containing gas. Operating conditions are not critical to the use of this invention, although temperatures are generally within the range of about 500° to about 1000° C. Gas/solid contacting steps may be performed according to any of the known techniques (e.g., the solids may be maintained as fixed beds, fluidized beds, moving beds, ebullating beds, etc.). Solids may be maintained in one contact zone or may recirculate between multiple contact zones (e.g., between oxygen contact and hydrocarbon contact zones).

METHANE CONVERSION PROCESS

One more specific application for the compositions of this invention is the conversion of methane to higher hydrocarbons. The process comprises contacting a gas comprising methane with a composition comprising a reducible metal oxide to produce higher hydrocarbons, coproduct water, and a composition comprising a reduced oxide of manganese. In addition to methane, the feedstock may contain other hydrocarbon or nonhydrocarbon components, although the methane content should typically be within the range of about 40 to about 100 volume percent, preferably about 80 to about 100 volume percent, more preferably about 90 to about 100 volume percent. Operating temperatures are generally within the range of about 500° to about 1000° C. Although not narrowly critical in the context of this invention, both total pressure and methane partial pressure affect results. Preferred operating pressures are within the range of about 1 to about 100 atmospheres, more preferably about 1 to about 30 atmospheres.

As indicated in the description of hydrocarbon conversion processes, a variety of process embodiments, including various gas/solids contacting modes, may be employed.

OXIDATIVE DEHYDROGENATION PROCESS

Another more specific application for the compositions of this invention is the dehydrogenation of dehydrogenatable hydrocarbons. The process comprises contacting a gas comprising a dehydrogenatable hydrocarbon with a composition comprising a reducible metal oxide to produce dehydrogenated hydrocarbons, co-product water, and a composition comprising a reduced oxide of manganese. Dehydrogenatable hydrocarbons include a wide variety of hydrocarbons (e.g., $C_2+$ alkanes, cycloalkanes, olefins, alkylaromatics, etc.). The dehydrogenated product depends in part on the feedstock selected. For example, alkanes may be dehydrogenated to form olefins, diolefins, alkynes, etc., and olefins may be dehydrogenated to form diolefins, alkynes, etc. One preferred class of feedstock comprises $C_2$–$C_5$ alkanes. One preferred process embodiment comprises oxidative dehydrogenation of $C_2$–$C_5$ alkanes to form the corresponding mono-olefins.

Operating temperatures are generally within the range of about 500° to about 1000° C. Operating pressures are not narrowly critical. In general, the process is conducted within the parameters of the oxidative dehydrogenation art, but uses a novel catalyst.

While the present invention has been described with respect to various specific embodiments, it is to be understood that the present invention is not limited thereto and that it can be variously practiced within the scope of the following claims.

What is claimed is:

1. A process for the conversion of methane to higher hydrocarbons and water which comprises contacting a feedstock containing methane at reactive conditions with a solid contact agent, said contact agent comprising:
   (a) a reducible metal oxide which produces higher hydrocarbons and water when contacted with said hydrocarbon at reactive conditions,
   (b) an oxide of zirconium; and
   (c) an oxide of yttrium,
and recovering product containing the higher hydrocarbons.

2. The process of claim 1 wherein said contacting is conducted at a temperature within the range of about 500° to about 1000° C.

3. The process of claim 1 wherein said zirconia comprises from about 1 to about 40 weight percent of said composition.

4. The process of claim 3 wherein said yttria comprises from about 1 to about 15 weight percent of said composition.

5. The process of claim 4 wherein said yttria comprises from about 2 to about 10 weight percent of said composition.

6. The process of claim 1 wherein said reducible metal oxide comprises manganese oxide.

7. The process of claim 6 wherein said manganese oxide comprises from about 5 to about 30 weight percent of said composition.

8. A process for the dehydrogenation of a dehydrogenatable hydrocarbon which comprises contacting a feedstock containing said hydrocarbon at reactive conditions with a solid contact agent, said contact agent comprising:
   (a) a reducible metal oxide which produces dehydrogenated hydrocarbons when contacted with said hydrocarbon at reactive conditions,
   (b) an oxide of zirconium; and
   (c) an oxide of yttrium, and recovering product containing a dehydrogenated derivative of said hydrocarbon.

9. The process of claim 8 wherein said contact is conducted at a temperature within the range of about 500° to about 1000° C.

10. The process of claim 8, wherein said zirconia comprises from about 1 to about 40 weight percent of said composition.

11. The process of claim 10 wherein said yttria comprises from about 1 to about 15 weight percent of said composition.

12. The process of claim 11 wherein said yttria comprises from about 2 to about 10 weight percent of said composition.

13. The process of claim 8 wherein said reducible metal oxide comprises manganese oxide.

14. The process of claim 13 wherein said manganese oxide comprises from about 5 to about 30 weight percent of said composition.

* * * * *